U S 012248046B2

United States Patent
Feiweier et al.

(10) Patent No.: US 12,248,046 B2
(45) Date of Patent: Mar. 11, 2025

(54) OPERATING A MAGNETIC RESONANCE DEVICE

(71) Applicant: Siemens Healthcare GmbH, Erlangen (DE)

(72) Inventors: Thorsten Feiweier, Poxdorf (DE); Andreas Greiser, Erlangen (DE); David Grodzki, Erlangen (DE); Bernd Kühn, Uttenreuth (DE); Mathias Nittka, Baiersdorf (DE); Dominik Paul, Bubenreuth (DE); Thorsten Speckner, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 2 days.

(21) Appl. No.: 16/744,171

(22) Filed: Jan. 15, 2020

(65) Prior Publication Data

US 2020/0225306 A1 Jul. 16, 2020

(30) Foreign Application Priority Data

Jan. 16, 2019 (EP) .................................. 19152127

(51) Int. Cl.
*G01R 33/54* (2006.01)
*A61B 5/055* (2006.01)
*G01R 33/385* (2006.01)

(52) U.S. Cl.
CPC ............ *G01R 33/543* (2013.01); *A61B 5/055* (2013.01); *G01R 33/385* (2013.01); *G01R 33/546* (2013.01)

(58) Field of Classification Search
CPC .. G01R 33/543; G01R 33/385; G01R 33/546; G01R 33/283; G01R 33/288; A61B 5/055
See application file for complete search history.

(56) References Cited

U.S. PATENT DOCUMENTS

2008/0024129 A1  1/2008  Heid
2009/0240379 A1  9/2009  Feiweier
(Continued)

FOREIGN PATENT DOCUMENTS

CN  101114013 A  1/2008
CN  101661087 A  3/2010
(Continued)

OTHER PUBLICATIONS

Bielmeier W. et al: "Optimierte Ausnutzung der maximalen Performanz der Leistungsverstärker einer MR-Anlage"; Prior Art Journal; Bd. 2015; Nr. 25; pp. 73-74; XP040672412; ISBN: 978-3-945188-28-6. with English Translation. pp 1-5.
(Continued)

*Primary Examiner* — Rishi R Patel
(74) *Attorney, Agent, or Firm* — Lempia Summerfield Katz LLC (57) ABSTRACT

A method for operating a magnetic resonance device is provided. The magnetic resonance device includes a component that has an operating limit in relation to a state parameter. The component uses a protocol to record magnetic resonance data. The protocol includes a magnetic resonance sequence and is described by protocol parameters. A protocol parameter set that, in relation to a protocol section, allows the protocol section to be repeated as often as desired without exceeding the operating limit is provided or determined. The method includes receiving a boost parameter from a user interface. At least for the protocol section, adaptation parameters are determined at least partially automatically based on the boost parameter, such that the desired number of repetitions described by the boost parameter is established while complying with the operating limit.

(Continued)

Magnetic resonance data is recorded with the protocol using the determined adaptation parameters.

19 Claims, 3 Drawing Sheets

(56) References Cited

U.S. PATENT DOCUMENTS

| | | |
|---|---|---|
| 2010/0090694 A1 | 4/2010 | Heid et al. |
| 2013/0090776 A1* | 4/2013 | Feiweier ................ G16H 40/20 700/295 |
| 2015/0285885 A1* | 10/2015 | Feiweier ................ G01R 33/36 324/309 |
| 2017/0156630 A1* | 6/2017 | Gabr .................... A61B 5/0037 |
| 2017/0254869 A1* | 9/2017 | Miyazaki ........... G01R 33/5619 |
| 2018/0038930 A1 | 2/2018 | Kroell |
| 2018/0143279 A1 | 5/2018 | Kluge |

FOREIGN PATENT DOCUMENTS

| | | |
|---|---|---|
| CN | 107693017 A | 2/2018 |
| DE | 102016222785 A1 | 9/2009 |
| DE | 102008015261 A1 | 5/2018 |

OTHER PUBLICATIONS

European Search Report for European Patent Application No. 19152127.7-1022 dated Aug. 2, 2019.

* cited by examiner

OPERATING A MAGNETIC RESONANCE DEVICE

This application claims the benefit of EP 19152127.7, filed on Jan. 16, 2019, which is hereby incorporated by reference in its entirety.

BACKGROUND

The present embodiments relate to operating a magnetic resonance device.

Magnetic resonance imaging has become an established medical modality. A multiplicity of possible imaging techniques, in which one or more different magnetic resonance sequences may be used in the context of protocols in order to record magnetic resonance data of an examination object (e.g., a patient), are available. This provides that protocol parameters that describe a protocol also include, for example, sequence parameters of the magnetic resonance sequences used therein.

The protocols and magnetic resonance sequences use various components of the magnetic resonance device, since at least one radio-frequency pulse is usually emitted for the purpose of exciting the examination region during the magnetic resonance imaging. A radio-frequency coil arrangement may be used for this purpose and may also be used for receiving the resulting magnetic resonance signals if a specific receiving coil arrangement is not provided for this purpose (e.g., as a local coil arrangement). The power for emitting radio-frequency pulses may be generated by a radio-frequency power amplifier (RFPA). Gradients are used for spatial encoding in magnetic resonance imaging, and the corresponding gradient fields are generated by a corresponding gradient coil arrangement that is in turn fed by a gradient power amplifier (GPA). In addition to the basic field magnets that are present in the main magnet unit, further components of the magnetic resonance device include, for example, shim coil arrangements, various cooling devices, and the like.

Such components take the form of hardware that, as a result of the respective configuration, may have power restrictions in relation to specific state parameters. For example, gradient-intensive magnetic resonance sequences require a multiplicity of gradient pulses that may cause a build-up of heat (e.g., in the gradient power amplifier itself, but also in other components of the magnetic resonance device). If an operating limit is reached for components thus heated (e.g., the gradient power amplifier), the corresponding component is to be switched off. The state parameter in this case is therefore the temperature, which is not to exceed a threshold value describing the operating limit. Therefore, magnetic resonance sequences or even protocols in general are to be configured such that overheating of the magnetic resonance device is prevented as far as possible.

Magnetic resonance sequences that require a high gradient power include, for example, echo planar imaging (EPI) sequences that may be repeatedly applied in the context of diffusion imaging, for example.

In the case of turbo spin echo (TSE) sequences, the problem that a high and possibly restrictive radio-frequency activity is required occurs in another example. A state parameter may relate to, for example, a loading of the radio-frequency power amplifier, such that in the case of, for example, lengthy or often rapidly repeated TSE sequences, flip angles of refocusing pulses may be reduced in order to provide that the radio-frequency power amplifier does not have to be switched off.

In other words, it is already proposed in the prior art to restrict adjustable protocol parameters for the magnetic resonance device to the extent that the examination (e.g., a specific protocol) may be performed without having to limit or switch off hardware components for protection and without adversely affecting the image quality as a result of falling below the powers required by the magnetic resonance sequence. Due to the complex dependencies within the individual protocol parameters, the specification of values for the protocol parameters that are only just possible and fully utilize the power output of the magnetic resonance device is often only possible by rolling out the complete measurement protocol or the magnetic resonance sequences contained therein, or, if applicable, only by rolling out the whole examination process in the case of an examination with multiple protocols.

In this context, it is already proposed in the prior art to model the influence of protocols on the system state in relation to the state parameter (e.g., using a state parameter model). Magnetic resonance sequences are rolled out within such a state parameter model in order to simulate effect on the state parameter. It is thus possible to estimate how long the magnetic resonance device may be operated at a specific power before the operating limit is reached. A clear example of this relates to heating up. Cooling devices of the magnetic resonance device may only carry away a finite quantity of heat. If due to demands on the gradient power amplifier or the radio-frequency power amplifier or other components more heat is supplied than the cooling device may carry away, the magnetic resonance device heats up and is to be switched off when the magnetic resonance device reaches an operating limit (e.g., a threshold value for the temperature). By simply observing the temperature state of the magnetic resonance device, it is therefore possible to summarize a multiplicity of aspects that contribute to the performance of the magnetic resonance device.

In order to reduce the complexity of the magnetic resonance device (e.g., also with regard to operation, in order therefore to design the use of the magnetic resonance device in a simple and reliable manner), magnetic resonances devices disclosed in the prior art follow the principle of unlimited repeatability of measurement protocols, also referred to as "run once, run ever" (RORE). This provides that magnetic resonance sequences are essentially configured in relation to the protocol parameters such that each measurement may be performed as often as desired and is not dependent on the initial system state of the magnetic resonance device. Even in the case of a magnetic resonance device that has already heated up, any RORE protocol may be performed because the RORE protocol does not result in any additional net heating that may lead to the operating limit being reached.

In another approach, protocols are specified such that the protocols may only be performed once ("run once" (RO)). This provides that protocol parameter sets that are thus specified utilize the power output of the magnetic resonance device to the extent that the state parameters are permitted to change as far as the operating limit. This provides that it is necessary to include the initial system state of the magnetic resonance device in the modeling process.

If the magnetic resonance device has already heated up, for example, no further measurement that would heat up the magnetic resonance device or the physically affected components beyond the operating limit may be performed. Since the magnetic resonance device cools down again in a state of rest, it is possible to determine the point when a given RO protocol may be performed again. The use of RO protocols may therefore be assisted by the introduction of measurement pauses, though this may significantly impair the measurement flow in some circumstances. Therefore, such approaches have not been pursued further until now.

Until now, the values of the protocol parameters allowed by the magnetic resonance device for a measurement have been so conservatively restricted that the power output of the magnetic resonance device may not generally be fully utilized. For example, it may be provided that only protocols according to the RORE approach may be used. This leads to suboptimal utilization of the available system performance, which is questionable in the light of increasing cost pressure for the hardware components used. Magnetic resonance devices that are capable of relatively high peak powers but may nonetheless only supply a more restricted nominal continuous power, which may further reduce the potential magnetic resonance data quality in the case of RORE protocols or further prolong the recording time, even though the magnetic resonance device would be fundamentally capable of significantly higher powers, have been proposed.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a way of better utilizing power output of a magnetic resonance device in the context of corresponding user demand is provided.

In one embodiment, a method includes receiving a boost parameter from a user interface. The boost parameter is selected by a user and describes an increased utilization of the power output of the magnetic resonance device while limiting the repeatability of the protocol section. At least for the protocol section, a processor determines adaptation parameters in a manner that is at least partially automatic based on the boost parameter, such that the desired number of repetitions described by the boost parameter is established while complying with the operating limit. The adaptation parameters include at least some of the protocol parameters. A controller records magnetic resonance data with the protocol, using the determined adaptation parameters.

A computer-implemented method that, relative to the concept of a protocol or protocol section that may be repeated as often as desired (e.g., without limit), uses a boost parameter that may be specified by a user in order to make an increased power output available for a specific measurement is provided. A protocol section in this context may in principle include the whole protocol, but the protocol section will more often include a magnetic resonance sequence or the respective protocol portion that involves particularly high demand (e.g., high-performance sequences; EPI sequences in the case of diffusion imaging), since other magnetic resonance sequences used in such a protocol result in significantly less gradient usage and therefore in significantly less heating up of components of the magnetic resonance device.

The strict RORE requirement may thus be deviated from for protocols that are to be performed; in response to demand from a user, a certain heating up of the magnetic resonance device or certain other change of a state parameter with respect to a system limit may be allowed. In this case, a protocol that is to be performed is assigned a boost parameter by the user, where the boost parameter defines how often it should be possible to measure the respective protocol before the operating limit is reached. According to an embodiment, the received boost parameter may directly describe the desired number. The default setting resulting in a RORE protocol would be a boost parameter of co (infinity) in this case, while a request for maximum power output of the magnetic resonance device would be given by a boost parameter of 1 (e.g., corresponding to an RO protocol).

By virtue of user-based specification of the boost parameter, it is possible over time for the user to learn what may be expected from the respective magnetic resonance device and what power gain may be achieved for various given examination objectives (e.g., if examination pauses occur between the examinations of different patients, within which the state parameters (the temperature) may substantially return to a basic level).

An example is provided by diffusion imaging in this case, for which protocols or protocol sections including an EPI sequence as a magnetic resonance sequence may require frequent repetition, such that a certain repeatability is entirely desirable. The boost parameter may then be selected accordingly such that the desired number corresponds to the maximum required number of measurements of the protocol section in the overall workflow of an examination. As explained in greater detail below, this applies in any case when the RORE condition is satisfied by other protocol portions beside the protocol section, such that unlimited repeatability applies there.

As described above, this may be the case if the protocol section contains at least the magnetic resonance sequence that has the greatest effect on the state parameters (e.g., the temperature). In the case of diffusion imaging, this relates to, for example, protocol portions in which an EPI sequence is used, since other sequences that are used in the context of the protocol or the examination generally (e.g., HASTE sequences or MPRAGE sequences) require significantly less gradient usage (e.g., only 5% of an EPI sequence), and therefore, a high-performance sequence may effectively be considered to represent the entire protocol. This also reduces the effort of determining the adaptation parameters, since, for example, it is not then necessary to roll out the entire protocol; it is sufficient to consider the intense portion of the high-performance sequence since the estimate in any case relates to a "worst-case scenario." Measurement pauses and the like occur in reality and allow the state parameter to normalize.

The present embodiments therefore allow improved utilization of the available hardware power output combined with the avoidance of complex dependencies over the entire examination flow, which would otherwise be produced by a simulation that encompassed the whole of the protocol of the power demand interacting with cooling phases and the like. In one embodiment, only a single boost parameter is used, and the parameter may be adjusted by the user, thereby providing the user with a simple intuitive implementation that again does not increase the complexity.

The adaptation parameters, which are ultimately specific selected protocol parameters relating to the protocol section, may be determined by relatively simple considerations in this case. The adaptation parameters are to be capable of adjustment. The adaptation parameters may be determined by identifying suitable modifications to the protocol section. For example, timing parameters may be considered as adaptation parameters (e.g., echo times (TE) and/or repetition times (TR)) in order to, for example, reduce cooling phases or make cooling phases available. Other parameters that may be considered relate to, for example, the flip angles, gradient magnitudes, and the like. Temporal sequences may also be changed. A multiplicity of possibilities exist for the selection of adaptation parameters that may depend, for example, on the desired effect of the improved utilization of power output.

Specifically, in order to determine the adaptation parameters, the response of the at least one state parameter may be simulated (e.g., by rolling out the protocol section and/or using a state parameter model). For example, the protocol events may be rolled out in order to show the influence on the at least one state parameter concerned (e.g., the temperature). Included in this may be modeling processes that may be implemented as easily as possible by a processor (e.g., linear state parameter models and/or other state parameter models of low complexity). For example, for a linear temperature model of the magnetic resonance device, the average gradient activity may be observed over a sliding window (e.g., a duration of six minutes). A number of possibilities are, however, already provided in the prior art for modeling and tracking the effects of protocols and magnetic resonance sequences on the system state of the magnetic resonance device, and these may also be used in the context of the present embodiments so that the influence of the protocol section on the state parameter may be estimated.

The determination of the adaptation parameters may be effected using a solution strategy and/or optimization method that is selectable (e.g., by a user). For example, the aim of an optimization method may be, given the desired number of repetitions of the protocol section, using the adaptation parameters such that the power output of the magnetic resonance device is so utilized as to arrive as close as possible to the operating limit. A certain safety margin relative to the operating limit may also be specified and complied with accordingly. The state parameter model may then, for example, be used to establish the extent to which a change in the state parameter towards the operating limit occurs when using current test values for the adaptation parameters, whereupon the test values may then be adapted until a termination criterion is reached as usual in optimization methods. In this case, optimization algorithms that are known from the prior art may also be used in the context of the present embodiments.

Since there may be complex dependencies between the various protocol/adaptation parameters and/or state parameters, as explained above, and the increased utilization of the power output may also be used in different ways, it is also effective in the context of the present embodiments to use specific solution strategies in order to be able to find optimal adaptation parameters, for example. In this context, it is possible, for example, to provide for the solution strategy to describe an objective (e.g., selected from the group including a reduction in the total time for performing the protocol, increasing the magnetic resonance data quality, and maximizing or minimizing at least one specific protocol parameter). For example, it has already been proposed in the prior art to introduce additional measurement pauses in order to allow a cooling of components of the magnetic resonance device, and therefore, for example, repetition times or the total examination duration have been lengthened. In order to shorten the duration of the measurement using the protocol, it is possible, for example, to aim at minimizing repetition times. Other aspects may aim at, for example, a higher image quality (e.g., by using bigger flip angles), increased gradients, and the like. The solution strategy may therefore ultimately define, for example, which adaptation parameters, optionally with which priority, are minimized or maximized. Combined approaches, in which different optimization objectives are pursued with different weightings, are also possible in this case. Exemplary solution strategies may include a minimization of the repetition time (TR), a minimization of the echo time (TE), or a minimization of the repetition time followed by the echo time.

In a further embodiment, the solution strategy may include a specification of value ranges that may be adjusted by a user for at least one adaptation parameter. For example, in the example cited above, maximum values for the echo time and the repetition time are specified. Unwanted extreme solutions in the solution set may therefore be avoided by the user. The solution strategy may also directly define adaptation parameters in a conclusive or non-conclusive manner. For example, a solution strategy may specify from the outset that the performance gain should be invested solely in a minimization of an echo time or a repetition time, or in a minimization of both parameters. For example, if a plurality of adaptation parameters are thus selected for optimization, the restriction of the permissible value range is particularly effective, especially with respect to maximum values for echo time and repetition time.

Precisely in the event of the specification of value ranges by a user, it may also occur that no conclusive solution may be found by applying the solution strategy (e.g., also if the current system state of the magnetic resonance device in relation to the state parameter is too unfavorable at the beginning of the protocol or protocol section), as discussed in greater detail below. In such cases, according to an embodiment, if the adaptation parameters may not be determined due to a conflict (e.g., an unsuitable initial system state and/or a user-specified value range that may not be complied with for an adaptation parameter), in order to establish the desired number of repetitions defined by the boost parameter while complying with the operating limit, as a conflict strategy, provision is made for at least one protocol parameter (e.g., a further protocol parameter) and/or the boost parameter to be adapted in order to resolve the conflict and/or for the solution strategy to be changed. For example, the conflict strategy may be specified and/or requested by a user via the user interface.

The present embodiments are intended to complicate the operation as little as possible for the user. In the simplest case, the user merely has to specify the boost parameter, of which there may be precisely one. The solution strategy, which is optionally adjustable, may define, for example, the adaptation parameters or combinations of adaptation parameters by which the potential power restriction is to be resolved. In the case of multiple adaptation parameters, as mentioned previously, an effective development of the present embodiments allows the value range for the adaptation parameters to be restricted by the user (e.g., by specifying an upper or lower limit value) depending on the adaptation parameters concerned. Any fundamental limitations of the magnetic resonance device or metrological restrictions are taken into account, and therefore, for example, indiscriminately short echo times or the like are impossible in any case. Following specification of at least the boost parameter, of which there may be precisely one, an internal reparameterization of the protocol takes place according to the boost parameter and the solution strategy, such that in most cases, no further user interaction is required and an optimized protocol may be generated in the background. Only in the event that selected values fail to provide a consistent solution for the adaptation parameters may a conflict strategy be requested for the purpose of resolving the conflict (e.g., in the form of an additional pop-up window).

For the purpose of simplifying the concept described here, it is essentially possible in this case to assume that between examinations, the additional parameters at least approximate specific starting values again, such that a defined initial system state of the magnetic resonance device may be presumed in relation to the state parameters. For example, it may be assumed that between two examination procedures for different patients, sufficient cooling of the magnetic resonance device takes place while the patients are swapped and/or the new patient is positioned.

In an embodiment, however, when determining the adaptation parameters, provision is made for taking into consideration a current system state of the magnetic resonance device in relation to the state parameter before the start of the protocol section (e.g., a current value of the state parameter before the start of the protocol section). In this way, it is also possible, for example, to take into consideration that the release of, for example, heat from the magnetic resonance device depends on the absolute current temperature, since the greater the temperature drop of the components towards the cooling medium of the cooling device, the more heat may be emitted by the components. It is therefore advantageous to take an initial state parameter into consideration when determining the adaptation parameters. In this case, the current system state may also be established between protocols or outside the protocol section, or predicted for the start of the protocol section. The current system state may be determined from measured values for the state parameter and/or by using the state parameter model and/or a further state parameter model. It is therefore possible, for example, to determine a temperature of the magnetic resonance device and/or at least a component using a suitable modeling process based on the protocol series (e.g., centrally in the control device of the magnetic resonance device). It is additionally or alternatively also possible to determine and use temperature values that are actually measured by temperature sensors provided on at least one heated component. It is not necessary in this case to take into consideration protocol portions that will be measured before the start of the protocol section and have little influence on the state parameter (e.g., by rolling out); it is instead also possible in such cases to assume that the current system state of the magnetic resonance device is still the current system state at the start of the protocol section.

If it should nonetheless occur that the protocol section has to be repeated more often than originally planned and therefore corresponding to the desired number, this need not necessarily signify a termination in the case of incomplete measurement. Instead, according to a development, if a number of repetitions of the protocol section as requested by the user and/or automatically triggered exceeds the desired number, the protocol parameter set for unlimited repetitions is used and/or a measurement pause is inserted for the repetitions after the desired number. Therefore, if contrary to expectations, the protocol section is to be repeated more often than the desired number (e.g., due to poor image quality as a result of patient movement), it is possible to directly use an equivalent protocol with RORE characteristics (and therefore inferior performance accordingly). Alternatively, an acceptable value of the at least one state parameter may be achieved again by a measurement pause (e.g., the magnetic resonance device may be cooled down to the extent that a further measurement of the protocol using the determined adaptation parameters becomes possible).

In the context of the present embodiments, it may effectively be provided that only magnetic resonance sequences that may be repeated as often as desired are used in protocol portions of the protocol that are located outside of the protocol section. Therefore, it may generally be assumed that only one protocol section with a high power demand will be used in a workflow, while all other protocol portions or magnetic resonance sequences may satisfy the RORE requirement.

In the context of the present embodiments, a plurality of protocol sections that may be assigned a boost parameter in each case may be defined in the protocol. Specifically, in the case of multiple protocol sections, it is possible to provide for the influence of the protocol section that was performed previously; the desired number of repetitions, on the initial system state of the magnetic resonance device in relation to the state parameter, may be taken into consideration at the start of the temporally subsequent protocol section. It is also possible here to take into consideration that the magnetic resonance device may cool down again between different protocol sections if, for example, RORE protocol portions are measured or measurement pauses occur between these protocol sections. In this case, it is possible, for example, for protocol portions to be suitably positioned within a workflow by the user or automatically, such that, for example, in the case of two protocol sections for which a higher power output will be used, one of these protocol sections may be positioned at the beginning of the overall protocol and one of the protocol sections may be positioned at the end of the protocol. Sufficient cooling or general resetting of the state parameter may thus take place in the meanwhile.

In most cases, workflows or protocols that describe an examination procedure of a patient include only one type of extremely power-intensive protocol sections, as indicated in the introduction; therefore, the typical application case of the present embodiments relates to the series of protocol sections in a compact time segment in the workflow (e.g., protocol sections with EPI sequences in the case of a whole-body diffusion measurement).

According to a development of the present embodiments, in the event that a protocol is interrupted by a monitoring unit of the magnetic resonance device due to an operating limit being exceeded, this protocol is continued or restarted using the protocol parameter set for unlimited repetitions. Magnetic resonance devices usually include monitoring units that may also be part of the control device of the magnetic resonance device and, when the operating limit is reached, perform an emergency stop, and may terminate a measurement that is currently taking place. The protocol may be continued with the protocol parameter set for unlimited (e.g., as frequent as desired) repetitions. The parameter set is specified such that even in the case of a magnetic resonance device that is operated close to the operating limit, this operating limit is not exceeded. Equivalent magnetic resonance data is still produced, but only with a longer time duration or reduced quality of the magnetic resonance data. The measurement is then nonetheless completed. As an alternative, the protocol may be restarted using the RORE protocol parameter set, though this may only take place after a corresponding request from the user. In all of the cases described here, it is, however, appropriate to inform the user about the incident via a corresponding output device. For example, if the protocol is continued with reduced utilization of the power output based on the RORE protocol parameter set, the effect of the measurement interruption is minimized since the previously measured magnetic resonance data may be used and simply supplemented by the remaining measurement in the RORE mode. The known present protocol parameter set for unlimited repetitions therefore offers a fallback level that may be used particularly advantageously in this context. It is therefore possible, for example, if some slices of the examination region have already been fully measured, to acquire the remaining slices with, for example, a reduced flip angle or an inferior slice profile, or with a longer repetition time or echo time.

As stated above, the state parameter may be a temperature of the component, for example. This applies to gradient-intensive magnetic resonance sequences, for example. Other state parameters are, however, also possible (e.g., a load state in a power amplifier device (a radio-frequency power amplifier device)) as a component. The protocol section may include a measurement with an EPI magnetic resonance sequence and/or a diffusion measurement and/or a measurement with a TSE sequence.

An embodiment is produced when applied to diffusion measurements (e.g., whole-body diffusion measurements) using EPI magnetic resonance sequences. In this case, a temperature may be considered as a state parameter (e.g., a temperature of the gradient coil arrangement and/or the gradient power amplifier device), where it has also proven effective to define a general temperature for the magnetic resonance device and to track this temperature in, for example, a state parameter model (e.g., a temperature model) for the magnetic resonance device as a whole. This latter averaging approach has already proven sufficient to successfully understand when operating limits are reached.

According to a possible development, if at least one protocol parameter may be adjusted by the user, provision may also be made for determining as a further adaptation parameter at least one extremal value that limits the user adjustment of one or more protocol parameters of the at least one protocol parameter. In other words, this provides that if the user concerned wishes to adjust protocol parameters, the user may specify a boost parameter in exactly the same way (e.g., directly the desired number of repetitions), such that the value ranges in which the protocol parameters are allowed to move may be determined automatically. Dependencies relative to other protocol parameters may exist here likewise and may result in dynamic updating of the specified extremal values. One or more of the present embodiments, however, are also aimed at increasing the useful power output of the magnetic resonance device in a manner that may be implemented as easily as possible by the operator.

In addition to the method, the present embodiments also relate to a magnetic resonance device including a control device (e.g., a controller) that is configured to perform the method according to the present embodiments. The control device includes the user interface, the controller, and the processor. All of the explanations relating to the method of one or more of the present embodiments may be applied analogously to the magnetic resonance device, which therefore also offers the advantages cited previously.

The control device may receive information from a user via the user interface (e.g., using a GUI). The received information includes, for example, a desired value of the boost parameter and optionally further information (e.g., value ranges for adaptation parameters, solution strategies, and the like), as described above. A processor in the context of the present embodiments signifies a processing unit generally, which may realize various functional subunits for different acts of the present embodiments (e.g., at least a determination unit for determining the adaptation parameters). Further, optional subunits may include, for example, a simulation unit in which it is possible to roll out at least the protocol section using the state parameter model. Multiple processors may also be provided. A processor may be a CPU or a GPU, for example.

A controller in the context of the present embodiments is understood to be a control unit. In this case, the controller includes at least a sequence unit that is therefore configured to record magnetic resonance data by applying corresponding magnetic resonance sequences in accordance with the protocol and receiving the corresponding magnetic resonance signals. The controller may be realized as at least one integrated circuit and/or including at least one chip, for example. The control device may additionally include at least one storage device (e.g., a memory).

A computer program according to the present embodiments may be loaded directly into a store of a control device of a magnetic resonance device, for example, and has program instructions for executing the acts of a method according to the present embodiments when the computer program is executed in the control device of the magnetic resonance device. The computer program may be stored on an electronically readable data medium according to the present embodiments and therefore includes electronically readable control information that is stored thereon. The control information includes at least a computer program as cited above and is embodied to perform a method according to the present embodiments when the data medium is used in a control device of a magnetic resonance device. The data medium is, for example, a non-transient data medium (e.g., a CD-ROM).

DETAILED DESCRIPTION

Figure 1:
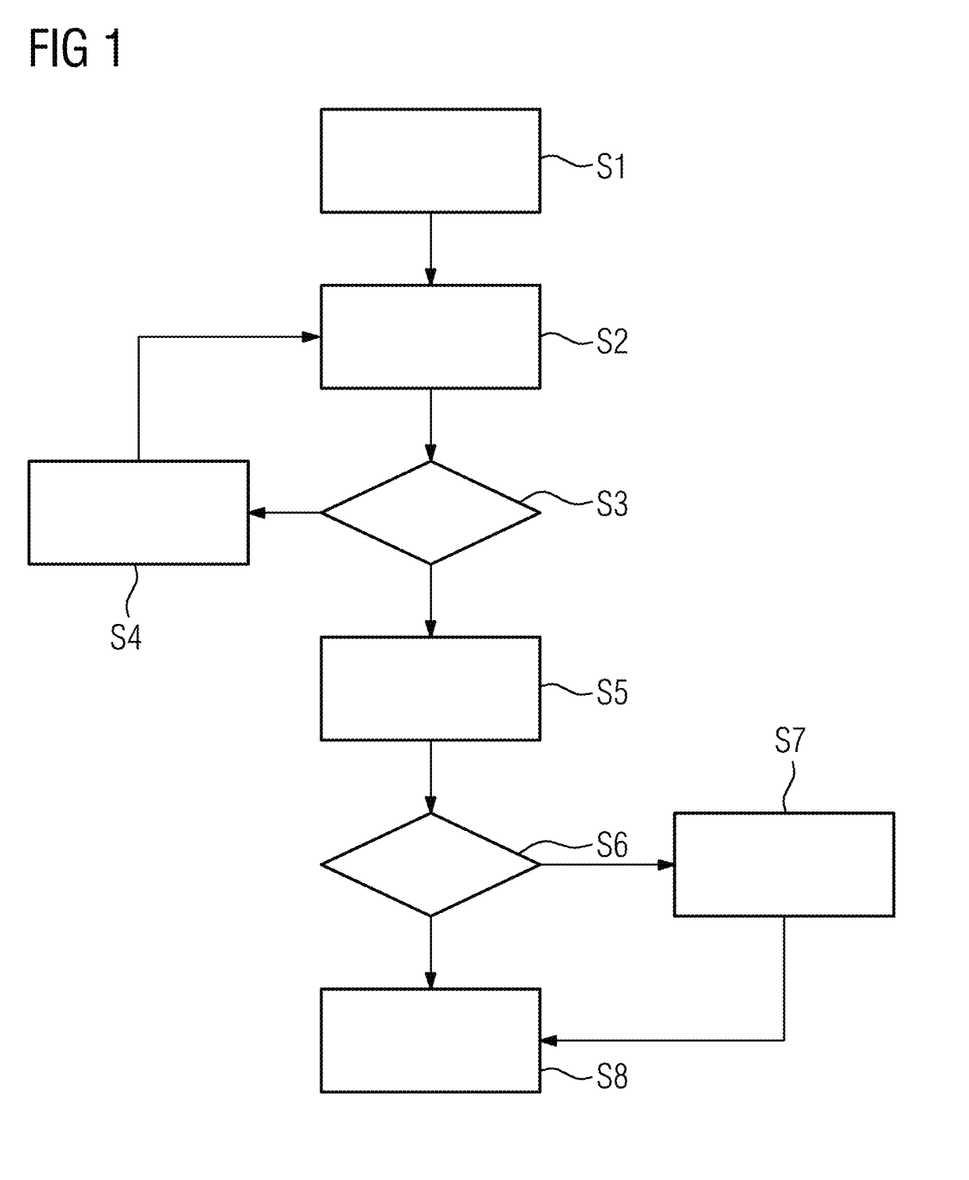
FIG. 1 shows a flow diagram of an exemplary embodiment of a method.

FIG. 1 shows a flow diagram of an exemplary embodiment of a method. As an example of an examination using a magnetic resonance device, reference is made in this case to a whole-body diffusion measurement. The whole-body diffusion measurement is described by a protocol that uses an EPI sequence as a magnetic resonance sequence in a protocol section. The EPI sequence places extremely high demands on a gradient power amplifier of the magnetic resonance device, such that heating up of the magnetic resonance device may occur when this protocol section is performed.

The magnetic resonance device includes components that are not to be overheated, and therefore, a system limit (e.g., in the form of a threshold value) exists as a state parameter for a temperature of the magnetic resonance device, where a live measurement is interrupted if the system limit is exceeded. In order to avoid such interruptions generally, a protocol parameter set containing protocol parameters for the protocol is stored in a control device of the magnetic resonance device and is used to provide an unlimited repeatability of the protocol, and, for example, therefore also of the protocol section, such that this protocol parameter set may therefore be designated as a run once, run ever (RORE) protocol parameter set.

The user may, however, selectively allow an improved utilization of the power output of the components of the magnetic resonance device in comparison with the RORE protocol parameter set (e.g., such that the measurement is accelerated and therefore pauses in the protocol provided for the purpose of cooling are largely avoided) using a boost parameter. A corresponding boost parameter, which in this case directly describes the desired number of possible repetitions of the protocol section (e.g., the presumed maximum repetitions necessary) may be input via a user interface. In the RORE scenario, the boost parameter has the value co (infinity), and therefore, each finite value for the boost parameter allows greater demand to be placed on the hardware components (e.g., the gradient power amplifier device).

Figure 2:
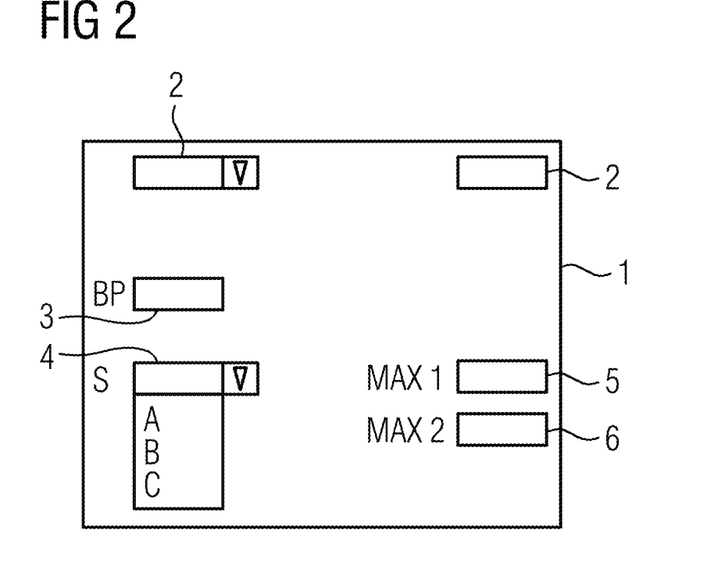
FIG. 2 shows an exemplary display for an implementation of a user interface.

The value desired by the user for the boost parameter is accepted via the user interface in the act S1 and therefore received in a processor. FIG. 2 shows a possible display 1 for implementing a graphical user interface (GUI) as a user interface. In addition to other operating elements 2, an input field 3 allows the boost parameter to be input (e.g., the desired number of repetitions (corresponds to the presumed maximum necessary number of repetitions)).

In the act S2 following thereupon, some of the protocol parameters of the protocol (e.g., adaptation parameters below) are determined again or adapted (e.g., taking the protocol parameter set as a starting point). The at least one adaptation parameter in this case relates, for example, to the EPI sequence and therefore, in general terms, to the protocol section. The present scenario is otherwise one in which the remaining protocol portions of the protocol beside the protocol section satisfy the RORE requirement.

In the act S2, a current system state of the magnetic resonance device in relation to the state parameter (e.g., the temperature) is taken as a starting point in order to determine, in the context of an optimization method for test values of the at least one adaptation parameter, effect on the state parameter (e.g., the temperature) in the magnetic resonance device. In other words, the protocol section is rolled out with the desired number of repetitions. The current system state of the magnetic resonance device (e.g., a type of initial temperature at the start of the protocol section) may already be established at any time, for example, using a state parameter model, but may also be specified at least in part from measured values supplied by temperature sensors of the magnetic resonance device.

The specification of optimal adaptation parameters in the present case is based on a solution strategy that may optionally also be specified by a user. For this purpose, as shown in FIG. 2, a drop-down menu 4 in which three solution strategies A, B and C may be selected in this case is provided in the graphical user interface. For example, the solution strategy A may represent a minimization of the echo time TE, B may represent a minimization of the repetition time TR, and C may represent a minimization of TE and TR. For example, if optimization is required in relation to two adaptation parameters, specifically the echo time TE and the repetition time TR, it is also effective to specify maximum values for the echo time and the repetition time in order to exclude unsuitable island solutions. This is possible for the user in this case using the input fields 5 and 6 as shown in FIG. 2, though these may also be completed automatically (e.g., with values that have been specified for the application case).

Other solution strategies may also be provided. For example, further adaptation parameters may be adapted, optionally including solution strategies that may be specified in more abstract terms (e.g., minimizing the total duration of the protocol and increasing the image quality).

In the present case, for the purpose of simulating the effects of current test values for the adaptation parameters, and therefore for the purpose of rolling out the repetitions of the protocol section, a simple temperature model is applied as a state parameter model, using general temperature data for the magnetic resonance device. For example, a linear model with a sliding time window may be applied using an average gradient. Other possibilities for state parameter models may be provided.

As mentioned above, it is assumed that other protocol portions beside the protocol section satisfy the RORE requirement and therefore influence the temperature as a state parameter only slightly in comparison with the protocol section; therefore, it is assumed it is sufficient here to roll out the protocol section in repetitions.

Act S3 checks whether the optimization method in the act S2, taking into consideration the solution strategy, the value ranges specified by the maximum values for the echo time and the repetition time, and the boost parameter, was able to find a solution. If this is not the case, a conflict, which may be attributed to the settings that have been made or to an unfavorable current system state, is present. In act S4, a pop-up window then asks the user how this conflict is to be resolved (e.g., by increasing the boost parameter, by choosing a different solution strategy, or by selecting a less optimal adaptation parameter). Following thereupon, it is again attempted in act S2 to find an optimal adaptation parameter set.

In act S5, the protocol parameter set that has been updated based on the adaptation parameter set is then used to record magnetic resonance data. In other words, the protocol is applied using the specified values for the adaptation parameters. As depicted by act S6, compliance with the operating limits is checked continuously in this case. If the temperature in act S6 exceeds the limit temperature despite the calculation performed in act S2, for example, or if it is established in act S6 that a greater number of repetitions is required than the desired number, the RORE protocol parameter set is used in act S7 as a fallback level (e.g., the measurement is continued using this RORE protocol parameter set in spite of any interruption that occurred as a result of reaching the operating limit). This provides equivalent magnetic resonance data, which may supplement the magnetic resonance data of the protocol that was already recorded using the adaptation parameter set and thereby effectively complete the measurement. There is no fear that the operating limit will be reached again or for the first time in this case, since the RORE protocol parameters are selected such that this cannot occur under normal operating conditions.

The end of the method is reached in act S8. The recorded magnetic resonance data may be postprocessed and/or stored and/or displayed as usual.

Figure 3:
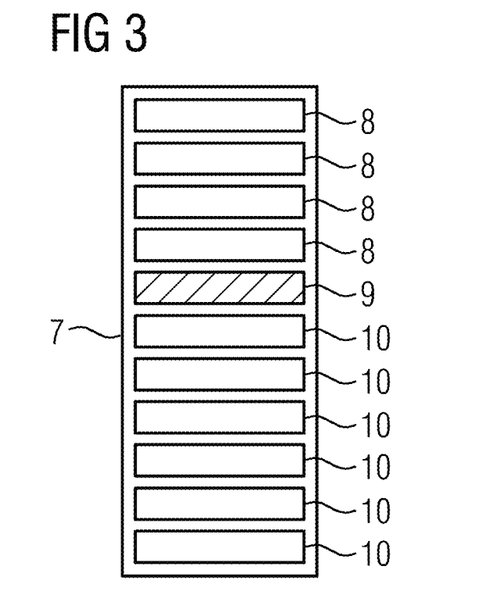
FIG. 3 shows flow of an exemplary protocol relative to time.

By way of example, FIG. 3 shows a possible flow of a protocol 7 for whole-body diffusion imaging. In the protocol portions 8 applied first, use is made of localizer sequences in order to record various localizer data for different body regions of the patient. These localizer sequences do not place any particular demand on the power output of the magnetic resonance device and are therefore classified in principle as RORE protocol portions.

Following thereupon, the protocol section 9 is performed with the repetition of the EPI sequences for the actual diffusion measurement. This portion is shown with hatched marking, since the portion represents that protocol portion of the protocol 7 that places by far the greatest demand on power. For example, the situation may be such that the protocol section 9 itself, in the RORE scenario, results in twenty times the power demand in relation to the gradient power amplifier in comparison with the other protocol portions 8, 10.

The subsequent protocol portions 10 relate to further recordings with other sequences (e.g., MPRAGE sequences, VIBE sequences and the like), which again have significantly lower power demands. The magnetic resonance data recorded there may be used for internal data processing purposes (e.g., correction algorithms) and/or for the purpose of producing anatomical magnetic resonance image data sets that may be used for the purpose of comparing or localizing diffusion phenomena, for example.

Figure 4:
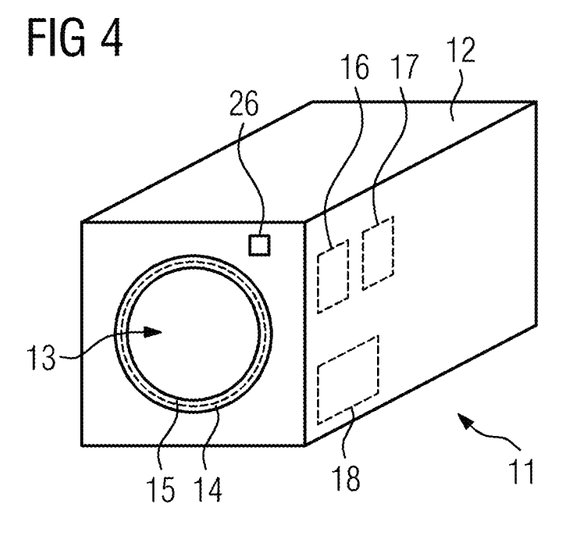
FIG. 4 shows a schematic diagram of one embodiment of a magnetic resonance device.

FIG. 4 shows a schematic diagram of one embodiment of a magnetic resonance device 11. As generally known, the magnetic resonance device 11 includes a main magnet unit 12. The main magnet unit 12 includes the basic field magnet and defines a patient chamber 13 into which the patient may be introduced by a patient couch that is not shown in detail here. Shown surrounding the patient chamber 13 in this case are a gradient coil arrangement 14 and a radio-frequency coil arrangement 15. Correspondingly, the magnetic resonance device 11 also has a gradient power amplifier device 16 and a radio-frequency power amplifier device 17 that may be located at least partly outside the screened cubicle in which the main magnet unit 12 is located. The operation of the magnetic resonance device 11 is controlled by a control device 18. A temperature of the magnetic resonance device 11 may also be captured via at least one temperature sensor 26.

Figure 5:
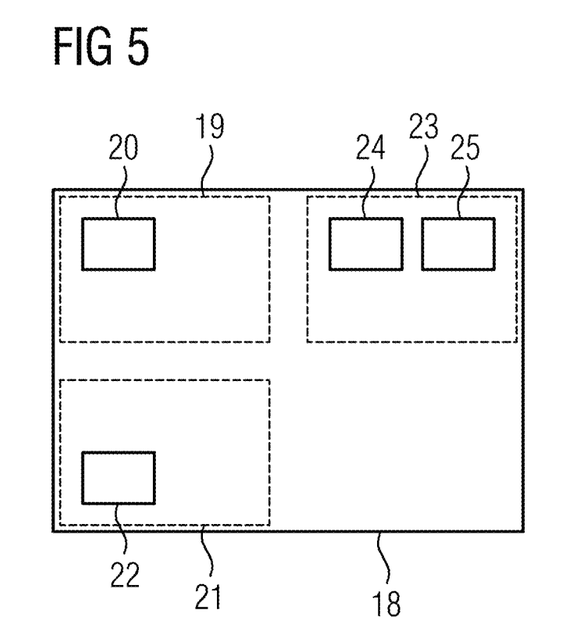
FIG. 5 shows functional structure of one embodiment of a control device of a magnetic resonance device.

FIG. 5 shows the functional structure of the control device 18 more precisely. This includes a processor 19 (e.g., a processing unit) that realizes in functional terms at least a determination unit 20 for performing the acts S2 and S3, but may also implement further computational functions within the control device 18. The interaction with a user takes place via a user interaction unit 21 that also implements the user interface 22. The user interaction unit 21 therefore contributes, for example, to the implementation of the acts S1 and S4.

The control device 18 further includes a controller 23 (e.g., a control unit) that incorporates at least one sequence unit 24 for performing the acts S5 and S7, and a monitoring unit 25 for performing the act S6.

Although the invention is illustrated and described in detail above based on exemplary embodiments, the invention is not restricted by the examples disclosed herein. Other variations may be derived therefrom by a person skilled in the art without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a magnetic resonance device, the magnetic resonance device comprising at least one component that has an operating limit in relation to a state parameter, the at least one component being for recording magnetic resonance data using a protocol that comprises at least one magnetic resonance sequence, wherein the protocol is described by protocol parameters, and a protocol parameter set that, in relation to a protocol section, allows the protocol section to be repeated as often as desired without exceeding the operating limit is provided or determined, the method comprising:

receiving a single boost parameter from a user interface, the single boost parameter being selectable by a user and describing an increased utilization of a power output of the magnetic resonance device while limiting a repeatability of the protocol section, the single boost parameter defining how often the protocol section is measurable before the operating limit is reached, the operating limit being related to a temperature of a component of the at least one component of the magnetic resonance device;

determining, by a processor and at least for the protocol section, adaptation parameters in a manner that is at least partially automatic based on the single boost parameter, such that a desired number of repetitions described by the single boost parameter is established while complying with the operating limit, the desired number of repetitions being at least two, the adaptation parameters comprising at least some of the protocol parameters; and recording, by a controller, magnetic resonance data with the protocol, using the determined adaptation parameters, wherein the received single boost parameter directly defines the desired number.

2. The method of claim 1, wherein determining the adaptation parameters comprises simulating a response of the state parameter.

3. The method of claim 2, wherein simulating the response of the at least one state parameter comprises rolling out the protocol section, using a state parameter model, or a combination thereof.

4. The method of claim 1, wherein the adaptation parameters are determined using a solution strategy, an optimization method that is selectable, or a combination thereof.

5. The method of claim 4, wherein the adaption parameters are determined using the optimization method, the optimization method being user selectable.

6. The method of claim 4, wherein the adaptation parameters are determined using the solution strategy, the solution strategy describing an objective.

7. The method of claim 6, wherein the objective comprises a reduction in a total time for performing the protocol, increasing a magnetic resonance data quality, or maximizing or minimizing at least one specific protocol parameter of the protocol parameters.

8. The method of claim 4, wherein when the adaptation parameters are not determinable due to a conflict, in order to establish the desired number of repetitions defined by the single boost parameter while complying with the operating limit, as a conflict strategy, at least one further protocol parameter, the single boost parameter, or the at least one further protocol parameter and the single boost parameter are adapted in order to resolve the conflict, the solution strategy is changed, or a combination thereof.

9. The method of claim 8, wherein the conflict comprises an unsuitable initial system state, a user-specified value range for one of the adaptation parameters that cannot be complied with, or a combination thereof.

10. The method of claim 1, wherein the adaptation parameters are determined taking a current system state of the magnetic resonance device in relation to the state parameter before a start of the protocol section into consideration.

11. The method of claim 1, wherein when a number of repetitions of the protocol section as requested by the user, automatically triggered, or as requested by the user and automatically triggered exceeds the desired number, a protocol parameter set for unlimited repetitions is used, a measurement pause is inserted for repetitions subsequent to the desired number, or a combination thereof.

12. The method of claim 11, wherein when the number of repetitions of the protocol section as requested by the user, automatically triggered, or as requested by the user and automatically triggered exceeds the desired number, the protocol parameter set for unlimited repetitions is used for repetitions subsequent to the desired number.

13. The method of claim 1, wherein only magnetic resonance sequences that are repeatable as often as desired are used in protocol portions of the protocol that are located outside of the protocol section, a plurality of protocol sections in the protocol to which the single boost parameter is assignable in each case are defined, or a combination thereof.

14. The method of claim 13, wherein in the case of the plurality of protocol sections, an influence of the protocol section that was previously performed with the desired number of repetitions on the initial system state of the magnetic resonance device in relation to the state parameter is taken into consideration at a start of a temporally subsequent protocol section.

15. The method of claim 1, further comprising:
interrupting, by a monitoring unit of the magnetic resonance device, the protocol due to the operating limit being exceeded; and
continuing the protocol or restarting the protocol using a protocol parameter set for unlimited repetitions after the protocol is interrupted.

16. The method of claim 1, wherein:
the state parameter describes a temperature of the at least one component, a load state in a power amplifier device as a component of the at least one component, or a combination thereof;
the protocol section comprises a measurement with an EPI magnetic resonance sequence, a diffusion measurement, a measurement with a TSE sequence, or any combination thereof,
or a combination thereof.

17. The method of claim 1, wherein the determining of the adaptation parameters comprises determining the adaptation parameters using a solution strategy that is selectable by a user, and
wherein the solution strategy describes an objective, the objective comprising a reduction in a total time for performing the protocol, increasing a magnetic resonance data quality, or maximizing or minimizing at least one specific protocol parameter of the protocol parameters.

18. A magnetic resonance device comprising:
at least one component that has an operating limit with respect to a state parameter, the at least one component being configured to record magnetic resonance data using a protocol that comprises at least one magnetic resonance sequence, wherein the protocol is described by protocol parameters, a protocol parameter set that, in relation to a protocol section, allows the protocol section to be repeated as often as desired without exceeding the operating limit, is providable or determinable;
a user interface;
a controller in communication with the user interface, the controller being configured to operate the magnetic resonance device, the operation of the magnetic resonance device comprising receipt of a single boost parameter from the user interface, the single boost parameter being selectable by a user and describing an increased utilization of a power output of the magnetic resonance device while limiting a repeatability of the protocol section, the single boost parameter defining how often the protocol section is measurable before the operating limit is reached, the operating limit being related to a temperature of a component of the at least one component of the magnetic resonance device; and
a processor in communication with the controller, the processor being configured to determine, at least for the protocol section, adaptation parameters in a manner that is at least partially automatic based on the single boost parameter, such that a desired number of repetitions of the protocol described by the single boost parameter is established while complying with the operating limit, the desired number of repetitions being at least two, the adaptation parameters comprising at least some of the protocol parameters,
wherein the received single boost parameter directly defines the desired number, and
wherein the controller is further configured to record magnetic resonance data with the protocol, using the determined adaptation parameters.

19. In a non-transitory computer-readable storage medium that stores instructions executable by one or more processors to operate a magnetic resonance device, the magnetic resonance device comprising at least one component that has an operating limit in relation to a state parameter, the at least one component being for recording magnetic resonance data using a protocol that comprises at least one magnetic resonance sequence, wherein the protocol is described by protocol parameters, and a protocol parameter set that, in relation to a protocol section, allows the protocol section to be repeated as often as desired without exceeding the operating limit is provided or determined, the instructions comprising:
receiving a single boost parameter from a user interface, the single boost parameter being selectable by a user and describing an increased utilization of a power output of the magnetic resonance device while limiting a repeatability of the protocol section, the single boost parameter defining how often the protocol section is measurable before the operating limit is reached, the operating limit being related to a temperature of a component of the at least one component of the magnetic resonance device;
determining, by a processor and at least for the protocol section, adaptation parameters in a manner that is at least partially automatic based on the single boost parameter, such that a desired number of repetitions described by the single boost parameter is established while complying with the operating limit, the desired number of repetitions being at least two, the adaptation parameters comprising at least some of the protocol parameters; and
recording, by a controller, magnetic resonance data with the protocol, using the determined adaptation parameters,
wherein the received single boost parameter directly defines the desired number.

* * * * *